United States Patent [19]

Bobichon et al.

[11] Patent Number: 4,858,652

[45] Date of Patent: Aug. 22, 1989

[54] PLUG FOR AN OPENING PROVIDING AN INSPECTION X-RAY SOURCE WITH ACCESS TO PIPEWORK OR TO AN APPARATUS

[75] Inventors: Jacques Bobichon, Verrieres le Buisson; Lucien Hervouin, Guyancourt; Gilbert Vigneron, Boulogne sur Seine, all of France

[73] Assignee: Societe Anonyme dite: Stein Industrie, Vezizy Villacoublay, France

[21] Appl. No.: 237,612

[22] Filed: Aug. 23, 1988

Related U.S. Application Data

[63] Continuation of Ser. No. 49,177, May 13, 1987, abandoned.

[30] Foreign Application Priority Data

May 13, 1986 [FR] France ................................ 86 06850

[51] Int. Cl.⁴ ............................................. F16L 55/10
[52] U.S. Cl. ........................................ 138/92; 138/89; 220/284
[58] Field of Search ........................... 138/89, 92, 155; 228/60, 119, 189, 263.15, 107; 29/402.09, 157.4; 378/59; 220/284, 288, 359, 361

[56] References Cited

U.S. PATENT DOCUMENTS

| | | | |
|---|---|---|---|
| 1,960,557 | 5/1934 | Snyder | 138/155 |
| 2,073,490 | 3/1937 | Lewin | 138/92 X |
| 2,209,975 | 8/1940 | Jacobus | 29/157.4 |
| 2,925,992 | 2/1960 | Rickard | 138/92 |
| 3,225,437 | 12/1965 | Stohr et al. | 228/103 |
| 3,945,431 | 3/1976 | Straub | 29/157.4 |
| 4,079,967 | 3/1978 | Schoesson | 378/59 |
| 4,203,185 | 5/1980 | Beyer et al. | 29/402.09 |
| 4,335,757 | 6/1982 | Lankston | 138/92 |
| 4,438,784 | 3/1984 | Bobichon et al. | 138/92 |

FOREIGN PATENT DOCUMENTS 566919 12/1958 Canada ................................ 138/92

Primary Examiner—James E. Bryant, III
Attorney, Agent, or Firm—Sughrue, Mion, Zinn, Macpeak & Seas

[57] ABSTRACT

A plug for an opening providing an inspection X-ray source with access to pipework or to an apparatus made of a high strength steel alloy which is fragile in welding, the plug comprising an open ended cylindrical component (6) which is welded (8) to the wall of the pipework or the apparatus, and which projects therefrom, said component being made of the same steel as the pipework or the apparatus, and a second cylindrical component (9) for closing the bore through the first component. The second cylindrical component is fixed to the outer end of the first component and in line therewith by means of a butt weld (10).

1 Claim, 1 Drawing Sheet

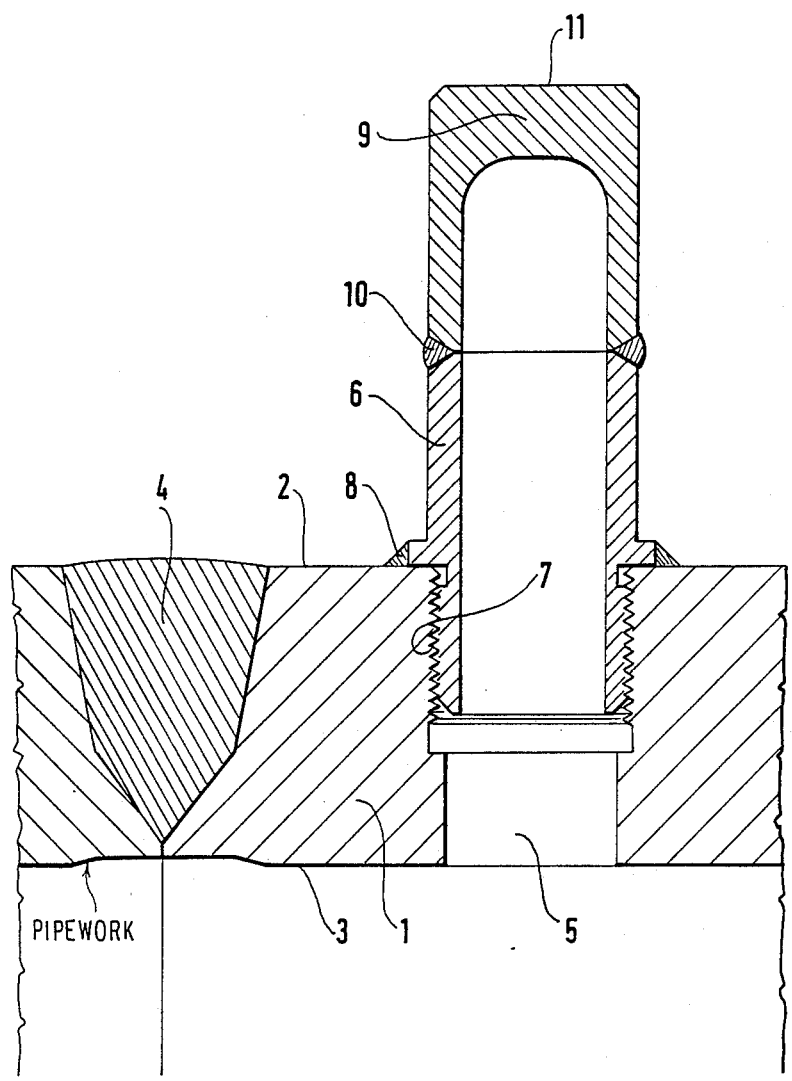

PLUG FOR AN OPENING PROVIDING AN INSPECTION X-RAY SOURCE WITH ACCESS TO PIPEWORK OR TO AN APPARATUS

This is a continuation of application Ser. No. 049,177, filed May 13, 1987, now abandoned.

The present invention provides a plug for an opening providing an inspection X-ray source with access to pipework or to an apparatus made of a high strength steel alloy which is fragile in welding, the plug comprising an open ended cylindrical component which is welded to the wall of the pipework or the apparatus, and which projects therefrom, said component being made of the same steel as the pipework or the apparatus, and a second cylindrical component for closing the bore through the first component.

BACKGROUND OF THE INVENTION

Stein Industrie's published French patent No. 2 507 778 (equivalent to U.S. Pat. No. 4,438,784) relates to a plug of this type, in which the first component includes an inside thread and the second component is an inner component having a solid end, having an outside thread which is screwed into the inside thread of the first component, which is lip-welded at its top edge or outside edge to said first component, and which includes internal means enabling it to be unscrewed.

Such a plug makes it possible to inspect welds in the pipework or the apparatus numerous times by means of an X-ray source inserted into the pipework or the apparatus by unscrewing the second component, and then by screwing it back into place after the weld has been inspected.

However, it is not possible to perform satisfactory lip-welding between the first and second components when the pipework or the apparatus is made of a high strength steel alloy since such alloys are very liable to crack after heat treatment, in particular after welding.

Preferred implementations of the present invention provide a plug for an opening providing an inspection X-ray source with access to pipework or to apparatus made of high-strength steel alloy and enabling a weld in said pipework or said apparatus to be inspected many times in spite of the susceptibility of such steels to cracking.

SUMMARY OF THE INVENTION

The present invention provides a plug of the type defined above, wherein the second cylindrical component is fixed to the outer end of the first component and in line therewith by means of a butt weld.

The first cylindrical component is preferably made of the same steel as the pipework or the apparatus, and the second cylindrical component is made of a steel having lower susceptibility to cracking. However, the second component may also be made of the same grade of steel as the pipework or the apparatus.

BRIEF DESCRIPTION OF THE DRAWING

A plug in accordance with the invention for an opening providing an inspection X-ray source with access to pipework is described below by way of example and with reference to the sole FIGURE of the accompanying drawing.

MORE DETAILED DESCRIPTION

The pipework 1 is made of high strength steel alloy. In particular, this steel may be the steel sold by Mannesmann Röhren-Werke AG corporation under the designation X 20 Cr Mo V 121, which contains 0.17% to 0.23% carbon, 0.10% to 0.50% silicon, 0.30% to 0.80% manganese, 11% to 12.5% chromium, 0.30% to 0.80% nickel, 0.80% to 1.20% molybdenum, and 0.25% to 0.35% vanadium, or the steel sold under the designation WSB 62 R by Thyssen Röhren-Werke AG corporation and comprising not more than 0.17% carbon, 0.25% to 0.50% silicon, 0.80% to 1.20% manganese, not more than 0.035% phosphorus, not more than 0.035% sulfur, 0.50% to 0.80% copper, 1% to 1.30% nickel, 0.25% to 0.40% molybdenum, and not more than 0.30% chromium.

The wall of the pipework 1 has an outside surface 2 and an inside surface 3. This pipework includes a weld fillet 4 whose compactness is to be inspected periodically by means of X-rays. A cylindrical hole 5 is made through the wall. A first plug component 6 is fixed in the bore of the hole by being screwed into a thread 7 in the outer portion of the bore. It is also fixed to the outside surface 2 of the wall by a circumferential weld 8.

The second component 9 of the plug is made of a steel which is less strong, and also less susceptible to cracking after welding, for example it may be from the steel sold under the name Chromesco 3 by Vallourec corporation and satisfying the following standards: AFNOR TU 10 CD 9-10 and DIN 10 CR Mo 9-10, comprising not more than 0.17% carbon, 0.20% to 0.70% manganese, not more than 0.035% phosphorus, not more than 0.035% sulfur, 0.05% to 0.55% silicon, not more than 0.30% nickel, 1.90% to 2.60% chromium, 0.85% to 1.15% molybdenum, not more than 0.25% copper, and 0.03% tin, with the tin percentage nevertheless being allowed to rise to as much as 0.04% if the quantity of (Cu+10Sn) does not exceed 0.55%. This second component has the same inside and outside diameters as the first component and is welded to the end thereof by a butt weld 10. It has a solid end 11.

When successive X-ray inspections are to be made of the weld 4, the following procedure is performed.

The first X-ray inspection is performed after the component 6 has been fixed in the hole 5 by screwing and then by circumferential welding 8. The X-ray probe is then removed and the second component 9 is welded onto the first component 6 by the butt weld 10.

When a new inspection is to be performed, the weld 10 is eliminated by grinding or by means of a tube-cutter. The probe can then be inserted and a new inspection performed. When the inspection is over, the probe is removed and the second component is welded back onto the first component by means of a new butt weld. The sealing of this butt weld can itself be inspected by X-rays without difficulty.

We claim:

1. In combination, a pipework (1) made of high strength steel alloy which is susceptible to cracking after heat treatment such as welding and which includes a wall, an opening (5) extending through said wall proximate a weld joint (4) of the pipework for providing an X-ray source with access to said pipework for the periodic inspection of said weld joint, said opening being threaded over at least a portion of its length from the outside of the pipework, and a plug for said opening, said plug comprising an open ended, first cylindrical component (6) having a central bore extending therethrough and having an outer threaded surface screwed into side wall opening and being welded (8) to an outer surface (2) of the wall, and projecting outwardly therefrom, said first cylindrical component being made of the same steel as the pipework, and a second cylindrical component (9) having a closed outer end (11) for closing the bore through the first component, an inner end of said second cylindrical component being butt welded (10) to an outer end of the first cylindrical component and disposed in axial alignment therewith, means allowing periodic weld joint inspections that are implemented by destroying the butt weld to enable the removal of the second cylindrical component, where thereafter the second cylindrical component is capable of being butt welded back onto the first cylindrical component, said allowing means comprising making said second cylindrical component of a steel having a lower susceptibility to cracking than that of the first component.

* * * * *